US006921264B2

(12) United States Patent
Mayer et al.

(10) Patent No.: US 6,921,264 B2
(45) Date of Patent: Jul. 26, 2005

(54) IMPLANT TO BE IMPLANTED IN BONE TISSUE OR IN BONE TISSUE SUPPLEMENTED WITH BONE SUBSTITUTE MATERIAL

(75) Inventors: Jorg Mayer, Niederlenz (CH); Marcel Aeschlimann, Ligerz (CH); Laurent Torriani, Biel (CH)

(73) Assignee: Woodwelding AG, Zurich (CH)

( * ) Notice: Subject to any disclaimer, the term of this patent is extended or adjusted under 35 U.S.C. 154(b) by 76 days.

(21) Appl. No.: 10/661,692

(22) Filed: Sep. 12, 2003

(65) Prior Publication Data

US 2004/0053196 A1 Mar. 18, 2004

Related U.S. Application Data

(63) Continuation-in-part of application No. 10/417,645, filed on Apr. 17, 2003.

(30) Foreign Application Priority Data

Aug. 23, 2002 (CH) .............................................. 1452/02

(51) Int. Cl.⁷ .............................................. A61B 17/68
(52) U.S. Cl. ........................................ 433/173; 433/174
(58) Field of Search ................................ 433/172, 173, 433/174, 175, 176

(56) References Cited

U.S. PATENT DOCUMENTS

| 772,029 A | 10/1904 | Clark |
| 2,366,274 A | 1/1945 | Luth et al. |

(Continued)

FOREIGN PATENT DOCUMENTS

| DD | 257797 | 2/1987 |
| DE | 2418198 | 4/1974 |

(Continued)

OTHER PUBLICATIONS

U.S. Appl. No. 10/415,454, filed Aug. 27, 2003, Aeschlimann et al.

(Continued)

Primary Examiner—Cary E. O'Connor
Assistant Examiner—Candice C. Stokes
(74) Attorney, Agent, or Firm—Rankin, Hill, Porter & Clark LLP

(57) ABSTRACT

An implant (1) to be implanted in bone tissue, e.g. a dental implant or an implant for an orthopedic application, comprises surface regions (4) of a first type which have e.g. osseo-integrative, inflammation-inhibiting, infection-combating and/or growth-promoting properties, and surface regions (8) of a second type which consist of a material being liquefiable by mechanical oscillation. The implant is positioned in an opening of e.g. a jawbone and then mechanical oscillations, e.g. ultrasound is applied to it while it is pressed against the bone. The liquefiable material is such liquefied at least partly and is pressed into unevennesses and pores of the surrounding bone tissue where after resolidification it forms a positive-fit connection between the implant and the bone tissue. The surface regions of the two types are arranged and dimensioned such that, during implantation, the liquefied material does not flow or flows only to a clinically irrelevant degree over the surface regions of the first type such enabling the biologically integrative properties of these surface regions to start acting directly after implantation. The implant achieves with the help of the named positive fit a very good (primary) stability, i.e. it can be loaded immediately after implantation. By this, negative effects of non-loading are prevented and relative movements between implant and bone tissue are reduced to physiological measures and therefore have an osseo-integration promoting effect.

48 Claims, 5 Drawing Sheets

U.S. PATENT DOCUMENTS

| | | |
|---|---|---|
| 2,458,152 A | 1/1949 | Eakins |
| 2,510,693 A | 6/1950 | Green |
| 2,942,748 A | 6/1960 | Anderson |
| 3,184,353 A | 5/1965 | Balamuth et al. |
| 3,481,803 A | 12/1969 | Hewitt |
| 3,499,222 A | 3/1970 | Linkow et al. |
| 3,612,803 A | 10/1971 | Klaas |
| 3,723,215 A | 3/1973 | Kessler |
| 3,919,775 A | 11/1975 | Malmin |
| 4,032,803 A | 6/1977 | Durr et al. |
| 4,100,954 A | 7/1978 | Muller et al. |
| 4,130,751 A | 12/1978 | Gordon |
| 4,248,232 A | 2/1981 | Engelbrecht et al. |
| 4,328,108 A | 5/1982 | Deeken |
| 4,360,343 A | 11/1982 | Hussein |
| 4,482,795 A | 11/1984 | Hinden |
| 4,525,147 A | 6/1985 | Pitz et al. |
| 4,566,138 A | 1/1986 | Lewis et al. |
| 4,675,972 A | 6/1987 | Bappert et al. |
| 4,717,302 A | 1/1988 | Adams et al. |
| 4,761,871 A | 8/1988 | O'Connor |
| 5,004,422 A | 4/1991 | Propper |
| 5,019,083 A | 5/1991 | Klapper et al. |
| 5,037,442 A | 8/1991 | Wintermantel et al. |
| 5,125,442 A | 6/1992 | Hendrickson |
| 5,163,960 A | 11/1992 | Bonutti |
| 5,167,619 A | 12/1992 | Wuchinich |
| 5,171,148 A | 12/1992 | Wasserman et al. |
| 5,244,933 A | 9/1993 | Eidenenz et al. |
| 5,271,785 A | 12/1993 | Devine |
| 5,308,205 A | 5/1994 | Lautenschlager |
| 5,393,559 A | 2/1995 | Shoesmith et al. |
| 5,413,578 A | 5/1995 | Zahedi |
| 5,426,341 A | 6/1995 | Bory et al. |
| 5,447,592 A | 9/1995 | Berce et al. |
| 5,547,325 A | 8/1996 | Tucker et al. |
| 5,562,450 A | 10/1996 | Gieloff et al. |
| 5,589,015 A | 12/1996 | Fusco et al. |
| 5,593,425 A | 1/1997 | Bonutti et al. |
| 5,709,823 A | 1/1998 | Hahn |
| 5,735,875 A | 4/1998 | Bonutti et al. |
| 5,752,831 A | 5/1998 | Padros-Fradera |
| 5,766,009 A | 6/1998 | Jeffcoat |
| 5,772,359 A | 6/1998 | Marty |
| 5,780,536 A | 7/1998 | Yokoyama et al. |
| 5,785,476 A | 7/1998 | McDonnell |
| 5,803,736 A | 9/1998 | Merritt, Jr. |
| 5,840,154 A | 11/1998 | Wittmaier |
| 5,871,514 A | 2/1999 | Wiklund et al. |
| 5,871,515 A | 2/1999 | Wiklund et al. |
| 5,897,578 A | 4/1999 | Wiklund et al. |
| 5,919,215 A | 7/1999 | Wiklund et al. |
| 5,941,901 A | 8/1999 | Egan |
| 5,964,764 A | 10/1999 | West, Jr. et al. |
| 5,993,458 A | 11/1999 | Vaitekunas et al. |
| 5,993,477 A | 11/1999 | Vaitekunas et al. |
| 6,007,539 A | 12/1999 | Kirsch et al. |
| 6,039,568 A | 3/2000 | Hinds |
| 6,056,751 A | 5/2000 | Fenton, Jr. |
| 6,059,817 A | 5/2000 | Bonutti et al. |
| 6,068,482 A | 5/2000 | Snow |
| 6,080,161 A | 6/2000 | Eaves, III et al. |
| 6,099,313 A | 8/2000 | Dorken et al. |
| 6,132,214 A | 10/2000 | Suhonen et al. |
| 6,139,320 A | 10/2000 | Hahn |
| 6,141,874 A | 11/2000 | Olsen |
| 6,193,516 B1 | 2/2001 | Story |
| 6,224,373 B1 | 5/2001 | Lee et al. |
| 6,273,717 B1 | 8/2001 | Hahn et al. |
| 6,332,885 B1 | 12/2001 | Martella |
| 6,545,390 B1 | 4/2003 | Hahn et al. |
| 6,592,609 B1 | 7/2003 | Bonutti |
| 6,635,073 B2 | 10/2003 | Bonutti |
| 2002/0044753 A1 | 4/2002 | Nagayama et al. |
| 2002/0077662 A1 | 6/2002 | Bonutti et al. |
| 2003/0118518 A1 | 6/2003 | Hahn et al. |

FOREIGN PATENT DOCUMENTS

| | | |
|---|---|---|
| DE | 3045706 | 12/1980 |
| DE | 3723643 A1 | 7/1987 |
| DE | 3828340 | 8/1988 |
| DE | 3919274 C1 | 6/1989 |
| DE | 9012044.2 | 8/1990 |
| DE | 9012548.7 | 9/1990 |
| DE | 4100636 A1 | 1/1991 |
| DE | 4209191 A1 | 3/1992 |
| DE | 4328108 | 8/1993 |
| DE | 0317757.7 | 11/1993 |
| DE | 19735103 A1 | 8/1997 |
| DE | 19741087 | 9/1997 |
| DE | 19916158 A1 | 4/1999 |
| DE | 19916160 A1 | 4/1999 |
| DE | 20113692 U1 | 8/2001 |
| EP | 0268957 | 6/1988 |
| EP | 0415615 | 8/1990 |
| EP | 0451932 A1 | 4/1991 |
| EP | 0534078 A1 | 7/1992 |
| EP | 0617935 | 10/1994 |
| EP | 1044655 | 3/2000 |
| EP | 1044656 A1 | 10/2000 |
| EP | 1184006 | 3/2002 |
| EP | 1 184 006 A2 | 3/2002 |
| EP | 1199049 | 4/2002 |
| FR | 1164445 | 1/1957 |
| FR | 1407582 | 9/1964 |
| FR | 1495999 | 10/1966 |
| FR | 2205402 | 11/1973 |
| FR | 2455502 | 5/1979 |
| FR | 2615786 | 5/1987 |
| FR | 0269476 | 10/1987 |
| GB | 762906 | 12/1956 |
| GB | 1203305 | 8/1970 |
| GB | 2061183 | 5/1981 |
| GB | 2277448 | 11/1994 |
| GB | 2324470 | 10/1998 |
| JP | 55121024 | 9/1980 |
| JP | 56139918 | 10/1981 |
| JP | 61104817 | 5/1986 |
| JP | 05245941 | 9/1993 |
| JP | 07222752 | 8/1995 |
| JP | 07300904 | 11/1995 |
| JP | 10323351 A1 | 12/1998 |
| WO | WO 88/03391 | 5/1988 |
| WO | WO 91/03211 | 3/1991 |
| WO | WO 94/18373 | 8/1994 |
| WO | WO 96/01377 | 1/1996 |
| WO | WO 96/37163 | 11/1996 |
| WO | WO 98/42988 | 10/1998 |
| WO | WO 01/09445 | 2/2001 |
| WO | WO 02/069817 | 3/2002 |
| WO | WO 02/38070 A1 | 5/2002 |
| WO | WO 02/087459 | 11/2002 |

OTHER PUBLICATIONS

Reader's Digest Complete Do–it–Yourself Manual (p. 69).
The Simon and Schuster Complete Guide to Home Repair and Maintenance (p. 45).
"Linear Vibration Welding of Non Metallic Components", Welding & Metal Fabrication, May 1989, pp. 152–154.

IMPLANT TO BE IMPLANTED IN BONE TISSUE OR IN BONE TISSUE SUPPLEMENTED WITH BONE SUBSTITUTE MATERIAL

BACKGROUND OF THE INVENTION

1. Field of the Invention

The Invention lies in the field of medical technology and relates to an implant that is implanted in human or animal bone tissue or in bone tissue supplemented with bone substitute material.

2. Description of Related Art

The implant according to the invention is, for example, a dental implant that, assuming the function of a natural tooth root, is implanted into a jawbone. In order to permit fastening of an artificial tooth crown, a bridge, or a dental prosthesis, the dental implant comprises, at its proximal end, a fixation location that, after implantation, is located in the region of the bone surface. The dental implant may represent a complete tooth replacement, that is to say may also have a crown region in addition to a root region to be implanted. The implant may also have a different function and may be suitable for implantation in another human or animal bone. Generally speaking, the implant serves for connecting a bone part with another tissue part, in particular with another bone part, or with an artificial part, which artificial part may support or replace a bone part (e.g., artificial joint) or a tooth or it may be a therapeutic auxiliary device (e.g., drug release device, drainage device, or stimulating device for electric or chemical stimulation). The implant may further be such therapeutic auxiliary device itself or it may serve for replacing missing bone tissue or possibly bone tissue to be regenerated (e.g. after removal of a tumor) or it may be an augmentation element for augmenting natural bone in a desired way.

Fixation of tooth replacement structures (individual teeth, groups of teeth, part-prostheses, or complete prostheses) based on the above mentioned dental implants with fixation locations is, according to the state of the art, realized in the following steps: after removal of the natural tooth root one waits until naturally regenerated bone tissue fills the opening in the jawbone. In the region of the regenerated bone tissue an opening adapted to the implant is created. The implant is positioned in the opening, wherein the opening is deep enough for housing the complete implant, which therefore does not protrude beyond the opening. An inner thread defining the fixation location at the proximal face of the implant is closed with a cover screw. The gum is closed over the cover screw and one waits until the bone tissue has ingrown with the implant and by way of this has a stability (secondary stability) sufficient for the loading to be expected. Then; in a further step, the gum is opened over the implant and the cover screw is replaced by a spacer, wherein the spacer projects beyond the gum. Only when the gum around the spacer is healed is the tooth replacement structure fastened on the implant. The briefly described procedure entails a treatment duration of twelve to eighteen months for the patient, of which two to three months fall in the time between the implantation and a point in time at which the bone tissue has grown around the implant or the implant is ingrown in the bone tissue such that the implant has sufficient stability for loading.

The first waiting period (regeneration of bone tissue in an opening in the jawbone) may be avoided or shortened if implants are used which in their shape are adapted as exactly as possible to the original opening, as for example described in the publication U.S. Pat. No. 6,132,214 (Suhonen et al.).

The dental implants according to the state of the art usually consist of pure titanium or of a titanium alloy. These materials exhibit a very good biological compatibility and there are various known surface designs that further improve osseointegration. Very often the implants also comprise macroscopic structures that permit the bone tissue to grow into or through the implant. However, the stability of these known dental implants is only adequate for full loading after complete osseointegration, i.e. only when they are intimately grown around by bone tissue or ingrown or intergrown with bone tissue (secondary stability). In osteoporotic or soft bone, as well as in poorly regenerating bone tissue, for example of older patients it may happen that no sufficient implant stability can be achieved.

The primary stability of the above-described dental implants, i.e. their stability directly after implantation, is greatly limited. For this reason the above mentioned waiting time is added between implantation and further build up. The primary stability of the mentioned implants varies according to implant form, but in most cases it is not sufficient for full loading. Pin-like implants with a thread are restrictedly loadable by tension and compression and possibly transverse forces, in particular when implanted such that at least one thread convolution lies in the region of the cortical part of the bone. They can hardly be loaded by torsion. Implants that do not have a round cross section, i.e. which are adapted to a natural tooth root, are more stable when loaded by torsion, but less stable when loaded by tension. The same applies to plate-like dental implants that may also comprise a plurality of fixation locations.

The un-sufficient loadability of known dental implants would, on loading immediately after implantation lead to movements between implant and bone tissue great enough for impeding or even preventing osseo-integration. However, immediate loading of implants is not only desirable in order to shorten the treatment duration, but also to avoid atrophy of the jawbone due to non-loading, i.e. to promote osseo-integration by way of micro-movements (not exceeding a physiological measure) between implant and bone tissue, which can only be achieved by loading a stable implant.

The primary stability, in particular the ability to be loaded in tension and compression is increased for pin-like implants according to the state of the art by way of a suitably formed threads (U.S. Pat. No. 3,499,222), by spread-out elements (e.g. U.S. Pat. No. 5,766,009, EP-1184006) or by collar-like elements. Anchor-like implants in particular used for fastening wires or sutures are equipped with barb-like surface structures (U.S. Pat. No. 4,360,343) for increasing the primary and secondary stability regarding tension loading. However, these improvements neither permit loading of the implants directly after implantation.

SUMMARY OF THE INVENTION

It is therefore the object of the invention to provide an implant suitable for implantation in bone tissue or in bone tissue being supplemented by bone substitute material, which implant has a very good primary stability, such that it is, for instance, able to be loaded immediately after implantation, which implant however is equipped for further clinical functions, e.g. for osseo-integration, for passage of particles or molecules into or out of the implant (delivery or drainage), for electric or chemical stimulation, etc., and this also immediately after implantation. The further clinical functions of the implant are not to suffer clinically relevant restriction by the wanted primary stability. If the implant has a load bearing function, i.e. if it is e.g. a dental implant, it is to be able to be loaded as unlimited as possible immediately after implantation or at least significantly earlier after implantation than known such implants. However, osseo-integration (further clinical function) remains substantially unhindered, i.e. begins immediately after implantation such that the above mentioned positive effects on osseo-integration effected by early loading can be fully exploited. Furthermore, neither the implant according to the invention nor its implantation is to be significantly more complicated than is the case for implants according to the state of the art.

The surfaces of the implant according to the invention, which are to come into contact with bone tissue or which are, for instance, to be grown around by bone tissue or are to be intergrown by bone tissue comprise regions of a first type and regions of a second type different from the surface regions of the first type.

The surface regions of the first type are equipped in a per se known manner for one or more than one predetermined clinical function. Examples of such clinical functions include the promotion or at least enablement of osseointe-gration for a good secondary stability, delivery of therapeutically effective compounds into tissue surrounding the implant, removal of unwanted compounds from tissue surrounding the implant (drainage), and electric or chemical stimulation of tissue surrounding the implant.

For an implant with a load bearing function, the surface regions of the first type comprise, for example, structures suitable for a stable ingrowth or through growth with vital bone tissue and they are, at least regarding osseo-integration, biologically active. Further or additional compounds having desirable effects, such as osseointegrative, inflammation-suppressing, infection-combating, and growth-promoting effects, may be delivered through the surface regions of the first type or these surfaces may be equipped for passage of therapeutically effective stimulating impulses.

The surface regions of the first type are, for example, biologically compatible surfaces (e.g. made of titanium) and they can be formed to have structures that are suitable for bone. tissue ingrowth. Such surfaces may further be coated with a material comprising calcium phosphate, they may be modified by phosphonates or peptide sequences, for example, and/or they may comprise gels or polymers containing growth factors.

The surface regions of the second type are designed for producing the primary stability. For this purpose these regions comprise a material that can be liquefied by mechanical oscillation, i.e. a material having thermoplastic properties (thermoplast or composite material comprising a thermoplastic component) or a thixotropic cement, wherein the liquefiable material is liquefied and pressed into unevennesses, pores or suitably produced geometries of the bone tissue surrounding the implant by application of mechanical oscillation (e.g. ultrasonic oscillation) during implantation.

The material constituting the surface regions of the second type forms part of the outer surface of the implant already before implantation or it is located on the inside of the implant and during implantation it is pressed in a liquefied state through corresponding openings to the outer surface of the implant, where it creates, in situ, the surface regions of the second type.

For the liquefied material of the surface regions of the second type to be able to be pressed into the bone tissue during implantation, the surface regions of the second type are arranged such that they come into contact with the bone tissue on positioning the implant in the bone. This means that the surface regions of the second type project, for example, at least locally beyond the surface regions of the first type or they are located at implant edges, projections, etc. For implants containing the material forming the surface regions of the second type inside, openings for pressing out the liquefiable material are arranged accordingly.

The surface regions of the two types are arranged and the liquefiable material and/or liquefaction are dimensioned such that the surface regions of the second type remain as free as possible of the liquefied material. This guarantees that the further clinical functions of the first type regions are not hindered or are hindered only to a clinically acceptable degree, even immediately after implantation. Therewith it is achieved that osseo-integration of surface regions of the first type is not only not hindered but is also not delayed and, therefore, starts immediately after implantation.

For implants which during implantation are moved relative to the bone tissue in an implantation direction, separation of the two types of surface regions is achieved by arranging the two types of surface regions next to one another and parallel to the implantation direction.

In the same way as known implants, the implant according to the invention is implanted in an opening specifically created for the implant possibly in beforehand regenerated bone tissue (e.g. of the jawbone) wherein this opening may accommodate the whole implant (root region) or wherein the implant in a self-cutting manner may be forced deeper than the opening into the bone tissue. The opening may, for example, only concern the cortical bone layer or, with a suitable design of the implant, it may be completely omitted. The implant according to the invention may also in the sense of a replica have a shape adapted to an irregular form of a bone cavity, e.g. the shape of a removed, natural tooth root and may be implanted directly into this cavity.

The implant according to the invention is, for example, a dental implant having the shape of a pin or of a natural tooth root and having at its proximal end a fixation location (e.g. pocket hole with an inner thread or location at which the dental surgeon may create such a pocket hole) or an artificial crown region. At its distal end it may be formed chisel-shaped and/or be provided with lateral self-cutting or grooving structures. It may furthermore be plate-shaped, disk-shaped, or blade-shaped and comprise one or more fixation locations, or it may have the shape of an anchor on which for example a wire or a suture can be fastened.

The implant according to the invention is of one piece and comprises the above-defined, different surface regions that, for example, consist of different materials, or it contains the liquefiable material inside and comprises openings through which the material when liquefied is pressed to the outer side of the implant. The implant may also be two-piece or multi-piece, wherein the surgeon combines two or more parts of various materials to form the implant.

For implantation, the implant according to the invention is positioned in the opening in the bone (or bone tissue supplemented with bone substitute material), e.g. in a jawbone, and then mechanical oscillation is applied to it, for example ultrasound, and simultaneously it is pressed against the bone. This causes at least part of the liquefiable material to be liquefied and pressed into pores, surface unevennesses and/or created geometries of the surrounding bone tissue, where after solidification it forms a positive-fit connection between the implant and the surrounding bone tissue or possibly bone substitute material. Depending on the implant design, the implant may also be advanced in the bone tissue (implantation direction) simultaneously to liquefaction.

For applying mechanical oscillation to the positioned implant, the sonotrode of an ultrasound apparatus is placed onto the proximal end of the implant. Experiments show that good results are achieved with a power of 0.2 to 20 W per square millimeters active surface. The frequency of the oscillations is between 2 and 200 kHz.

Implants according to the invention and having a load bearing function (e.g. dental implants) comprise a central implant part carrying the surface regions of the first type and being made of metal (e.g. steel, titanium, cobalt/chromium alloy), of a ceramic or glass-like material (e.g. aluminum oxide, zirconium oxide, ceramic or glass of calcium phosphate), of a thermoset or high-temperature thermoplastic polymers (Polyether arylketones, Polyfluoro- or polychloroethylenes, polyether imides, polyether sulphones, polyvinylchloride, polyurthanes, polysulphones, polyesters) or of a composite material (e.g. high-temperature thermoplast reinforced with carbon fibers). Such implants also comprise a peripheral implant part of the liquefiable material, for example of a material with thermoplastic properties. The liquefiable material may also be placed on the inside of a hollow, central implant part, wherein the walling of the central implant part has through openings through which the liquefied material is pressed under the influence of the mechanical oscillation, in order to form surface regions of the second type on the outside of the walling. The implant parts may be connected to one another on the part of the manufacturer or only be brought into connection with one another by the surgeon directly before or during implantation.

Implants according to the invention which have no relevant load bearing function (e.g. implants having a delivery function, a drainage function, or a stimulating function) may also comprise a central implant part and a peripheral implant part, the peripheral implant part consisting at least partly of the liquefiable material, wherein the mechanical stability (load bearing function), which is necessary for implantation may be taken over by the peripheral implant part, the central implant part having but very little mechanical-stability. Such a central implant part is e.g. a permeable container e.g. of porous calcium phosphate or of an other bone substitute material having little mechanical stability or of a thin membrane, wherein delivery or drainage or simulation takes place through the container wall. The central implant part may also be a body of porous calcium phosphate or of another bone substitute material and have the function of initiating or assisting formation of missing or additionally desired bone tissue. It is possible to provide the liquefiable material on the inside of the central implant part and press it when liquefied through corresponding openings to the outer surface of the central implant part, even if the latter implant part has little mechanical stability.

The implant according to the invention may also consist of only one material that is able at the same time to fulfill the demands with regard to the mechanical strength of the implant and possibly of a fixation location, the demands set by the further clinical functions of the surface regions of the first type (e.g. biological integration or secondary stabilization respectively) and the demand of the liquifiability by mechanical oscillation. As the case may be, in various regions of the implant the one material may be filled to varying degrees (e.g. with fibers, whiskers, or particles) or it may be filled with different materials in different regions. In this case too, a suitable design of the surface regions to be integrated in the bone tissue must ensure that, upon implantation, the surface regions of the second type or the liquefied material respectively comes into contact in particular with the bone tissue and that the liquefied material is not or only to a clinically irrelevant degree carried onto the surface regions of the first type.

For implants with surface regions equipped for osseointegration, the liquefiable material is advantageously at least partly biologically degradable (resorbable) so that the stability function (primary stability) of the positive fit between the implant and the bone tissue is gradually taken over by the stability function (secondary stability) of the osseo-integration, which advantageously increases to the same degree as the liquefiable material is resorbed, i.e. the primary stability decreases. In particular in the case of osteoporotic bone tissue or poorly regenerating bone tissue it may be advantageous to permanently retain the primary stabilization as a supplement to the secondary stabilization, i.e. to use a non-resorbable, liquefiable material, which may also be equipped for good biological integration (secondary osseointegration).

For implants with other than load bearing functions, the liquefiable material is advantageously at least partly resorbable, if the implant is to be removed from the bone tissue or to be completely replaced by bone tissue. If the primary stability is to be retained, the liquefiable material is not resorbable or only partly resorbable.

Resorbable polymers such as those based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplasts such as, for example, polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers or corresponding copolymers or blended polymers or composite materials containing the mentioned polymers as components are suitable as non-resorbable polymers. Applicable thixotropic systems are resorbable, partly resorbable, or non-resorbable polymeric, ceramic or hydraulic cements (e.g. Norian® of Synthes or Sulfix® of Centerpulse).

The liquefiable material may contain foreign phases or compounds serving further functions. In particular, the liquefiable material may be strengthened by admixing fibers or whiskers (e.g. of calcium phosphate ceramics or glasses) and such represent a composite material. The liquefiable material may further contain components that expand or dissolve (create pores) in situ (e.g. polyesters, polysaccharides, hydrogels, sodium phosphates) or compounds to be released in situ and having a therapeutic effect for promotion of healing and regeneration (e.g. growth factors, antibiotics, inflammation inhibitors or buffers such as sodium phosphate against adverse effects of acidic decomposition). If the liquefiable material is resorbable, release of such compounds is delayed.

The implant part not comprising the liquefiable material is not resorbable, if the implant is to remain in the patient's body or if it is to be removed surgically. However, this implant part may also be made at least partly of a resorbable material, which after implantation is gradually replaced by vital tissue.

The design of the implant and the selection of the liquefiable material are to be matched to one another such that the strength of the positive fit is sufficient for the expected loading, and such that liquefaction entails a reasonable, that is to say, a low as possible heat release. If liquefiable materials with a relatively high softening temperature are used, it is advantageous to ensure that the implant as a whole (including liquefiable material) conducts the mechanical oscillations as a resonator so that the liquefiable material is liquefied in the surface regions of the second type only very locally, e.g. only in regions of suitably provided energy directors. In this manner the released quantity of heat can be kept to within an acceptable scope. In particular, when using a material with a relatively low softening temperature or a material being liquefiable without release of heat (e.g. thixotropic cements), liquefaction may also be effected in the inside of the liquefiable material (by large damping of the exciting oscillation) or at contact locations between the central and peripheral implant part.

The heat burden on the tissue during implantation may be reduced even further by designing the central implant part to comprise materials with a large heatconducting capability and/or a large thermal capacity (e.g. silicon carbide) and, as the case may be, to comprise cooling channels through which a cooling medium flows.

BRIEF DESCRIPTION OF THE DRAWINGS

Exemplary embodiments of the implant according to the invention are described in detail by way of the following Figures, wherein:

FIG. 8: cross section);

FIG. 12: plan view);

DETAILED DESCRIPTION OF THE PREFERRED EMBODIMENTS

Figure 1:
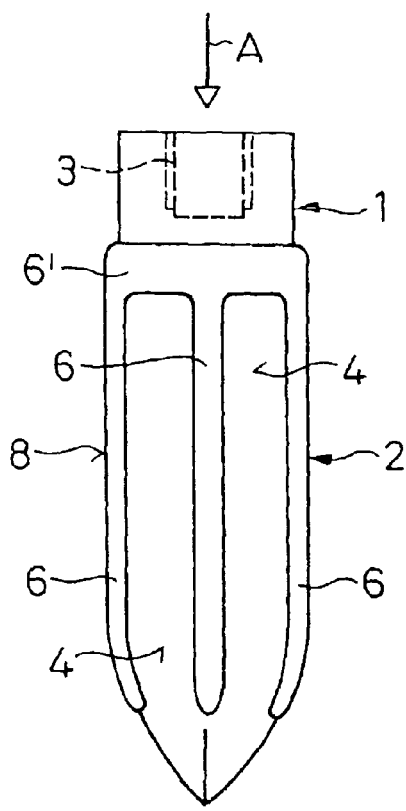
FIGS. 1, 2A, 2B, 2C show three first exemplary embodiments of a substantially pin-shaped implant according to the invention (e.g. dental implant), the implants comprising a central and a peripheral implant part, (FIG. 1: side view, FIGS. 2A to 2C: cross sections)

FIGS. 1 and 2A to 2C show an exemplary, pin-shaped embodiment of the implant according to the invention, which implant has a load bearing function and therefore is, for example, a dental implant or an orthopedic implant serving for stabilizing a bone fracture or for fixing a support plate or as a shaft of an artificial joint part (e.g. hip, knee, shoulder or finger joint). The implant comprises a central implant part 1 and a peripheral implant part 2, wherein the central implant part comprises at its proximal end a fixation location 3 (e.g. pocket hole with inner thread or location at which a surgeon may create such a pocket hole). The distal implant end is chisel-shaped for a self-cutting effect. The implant may also, as illustrated in the cross section according to FIG. 2C, comprise axially extending, self-cutting or grooving elements 9.

The central implant part 1 comprises surface regions 4 of the first type (e.g. with osseo-integrative, inflammation-inhibiting, infection-combating and/or growthpromoting properties) extending parallel to the implantation direction A. Between the surface regions 4 of the first type, the implant comprises surfaces that are suitable for connection to the peripheral implant part 2. The connection between the peripheral implant part 2 and the central implant part may be an adhesive connection 5 (FIG. 2A) or a positive fit connection, e.g. individual grooves 5' (FIGS. 2A and 2C) with a narrowed opening slot or surfaces 5" with a multitude of openings or grooves (FIG. 2B). The peripheral implant part 2 comprises fingers 6 that, for example, fit into the grooves 5' or onto the surface regions 5" and that form at least part of the surface regions 8 of the second type.

Figure 2A:
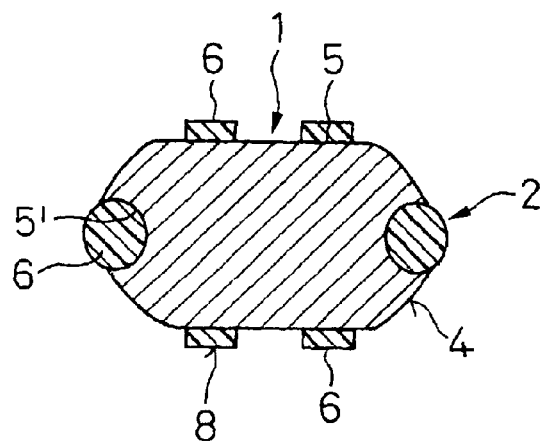
Figure 2B:
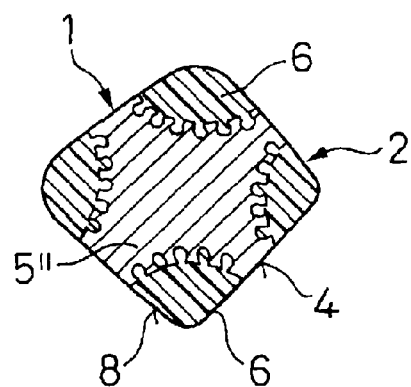
Figure 2C:
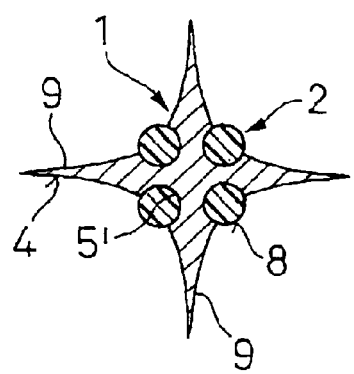

As seen in FIGS. 2A to 2C, the invention does not set any conditions on the cross section of the pin-shaped implants so that this may be selected depending on the function. Therefore, cross sections other than those shown in the three FIGS. 2A to 2C are conceivable, for example a central implant part with a round cross section and fingers 6 seated thereon, as shown in FIG. 2A.

The implant illustrated in FIG. 2C may in particular be driven into the bone tissue for example in a largely self-cutting manner. For preventing the liquefied material from being driven onto the surface regions 4 of the first type, the surface regions of the first and of the second type (4 and 8) extend next to one another and parallel to the implantation direction A. In the proximal region where the implantation path is only short, the fingers 6 may open out into a ring 6' extending around the central implant part 1 and advantageously held in a groove of the central implant part. The ring 6' not only groups the fingers 6 together into a coherent, peripheral implant part 2, which is advantageous for easy connection of the two parts possibly by the surgeon, but also constitutes a means for intimate primary stabilization between the implant and the cortical bone tissue in particular against tension and torsion. Where appropriate, a thread or a similar structure is created in the cortical bone so that the ring 6' can be connected to this relatively compact bone layer by a positive fit.

For an implant to be positioned in a deeper opening and not to be displaced or only slightly during oscillation, the surface regions of the first and second type may be arranged differently. The surface regions 8 of the second type may form, instead of fingers 6, a pattern of points or intersecting lines. The arrangement of the surface regions 8 of the second type is thus to be adapted to the manner of implantation. Furthermore, the arrangement of the second type surface regions is to be adapted to the primary stability to be achieved by the liquefied material, i.e. the primary stability that cannot be achieved by the implant shape.

The two implant parts 1 and 2 of the implants shown in FIGS. 1 and 2A to 2C may be connected to one another by the manufacturer. The peripheral implant part 2 may, for example, be manufactured by injection molding directly on the central implant part 1. The two implant parts 1 and 2 may also be manufactured separately and joined together by the surgeon directly before the implantation. In this case it is advantageous to realize the positive-fit or adhesive connection between the two materials during the implantation in that the material of the peripheral implant part 2 is liquefied and, for example, is pressed into openings or grooves according to FIG. 2B of the central implant part. For this it may be necessary to provide the inner side of the peripheral implant part 2 or the corresponding surface of the central implant part 1 with energy directors.

The advantage of the joining-together by the surgeon lies in the fact that the two parts can be sterilized separately, i.e. possibly using different methods being adapted to the various functionalities of the parts. Sterilization of the whole implant is then not necessary. The joining-together just before implantation allows the manufacturer to make available a set of central implant parts differing from one another. For example, the central implant parts may vary with respect to length and diameter and peripheral implant parts differing for example with respect to material or finger thickness, so that the surgeon may himself put together a suitable implant exactly for the case in question (greater variability at lower number of components).

For implanting the pin-shaped implants according to FIGS. 1 and 2A to 2C an implantation device (e.g. sonotrode of an ultrasonic device) is used, which device has a distal end substantially adapted to the proximal face of the implant. If necessary, a coupling piece is introduced between sonotrode and implant. The oscillation energy is advantageously applied to the central implant part.

Figure 3:
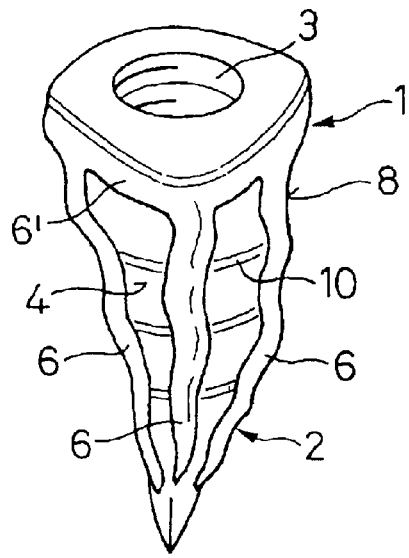
FIG. 3 shows a second exemplary embodiment of the implant according to the invention (e.g. dental implant), the implant comprising a central and a peripheral implant part, wherein the shape of the implant is adapted to an existing cavity in a bone (e.g. cavity caused by removal of a natural tooth root from a jawbone)

FIG. 3 shows a dental implant according to the invention which in principle is designed in a similar way as the implant according to FIG. 1 but takes its shape not from the known pin-like or screw-like implants, but rather from a natural cavity in a bone, in the illustrated case from an natural tooth root. Between the surface regions 8 of the second type, which are formed by the peripheral implant part 2, i.e. in the surface regions 4 of the first type, the central implant 1 is provided with structures permitting like a thread an improved anchoring in the regenerated bone tissue (secondary stability).

Figure 4:
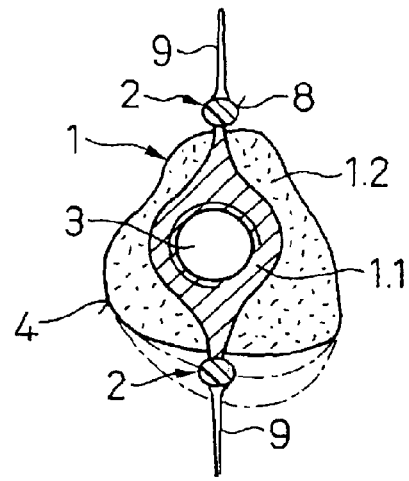
FIGS. 4 and 5 show two further embodiments of the implant according to the invention (e.g. dental implant), the implant comprising a central and a peripheral implant part, wherein the central implant part is adapted to an existing cavity in a bone (e.g. is an imitation of a natural tooth root) and is designed to be self-cutting or grooving (cross section)
Figure 5:
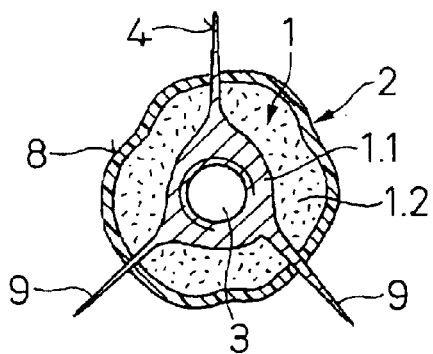

FIGS. 4 and 5 show in cross section two further embodiments of the implant according to the invention, which are suitable for being implanted in existing bone cavities, e.g. in a cavity created by removal of a natural tooth root. The implant is adapted to a specific cavity and comprises axially extending, self-cutting or grooving elements 9. The central implant part 1 of the two implants consists of a pin part 1.1 (load bearing part) that carries a fixation location 3 or an artificial tooth crown and a body part 1.2. The body part 1.2 is shaped ex situ in the sense of a replica, for example using the removed tooth root, such as described in the publication U.S. Pat. No. 6,132,214 (Suhonen et al.), or in situ, i.e. in the corresponding cavity.

The body part 1.2 according to FIG. 4 forms the surface region 4 of the first type (e.g. with osseo-integrative, inflammation-inhibiting, infection-combating and/or growth promoting properties) and consists of an advantageously resorbable or partly resorbable bone substitute material (e.g. calcium phosphate, polylactide, nonresorbable polymer filled with calcium phosphate, combination system with reinforcing elements). The peripheral implant part 2 is limited to the self-cutting or grooving elements 9 into which, for example, pin-like parts of the liquefiable material are introduced.

The implant according to FIG. 4 may be implanted in two successive steps. Firstly the existing cavity is filled with a piece of a bone substitute material (body part 1.2). Then the pin part is implanted wherein the anchorage through the liquefiable material (peripheral implant part 2) may effect at least partly the bone substitute material. Such cases are illustrated in FIG. 4 by dash dot lines.

The body part 1.2 according to FIG. 5 is formed by a relatively thin and as flexible as possible layer of the liquefiable material, i.e. is surrounded by the peripheral implant part 2 that forms the surface of the second type. Instead of the thin layer, a membrane, which is at least partly coated with the liquefiable material, may also be provided. The axially extending, self-cutting or grooving elements 9 comprise the surfaces 4 of the first type. The body part 1.2 consists of a plastic, curable material, for example a bone cement that may be cured by light, ultrasound, or heat or of a hydraulic cement, which cement preferably has thixotropic properties. On introduction into the cavity, the body part 1.2 takes the shape of the cavity. On applying mechanical oscillations not only is the liquefiable material of the surface regions of the second type pressed into pores and unevennesses of the surrounding bone tissue but also the body part is adapted to the shape of the cavity and is possibly also cured. The liquefiable material is advantageously resorbable so that the primary stability created by the surface regions 8 of the second type is taken over by a secondary stability which is firstly caused by osseo-integration of the body part 1.2 and on resorption of the body part by osseo-integration of the pin part 1.1.

Implants according to FIGS. 4 and 5, which are designed as dental implants, may be implanted in the jawbone essentially directly after removal of a natural tooth root because their shape is adaptable to the cavity created by the removal. Thanks to the primary stability achieved by the surface regions 8 of the second type they may also be loaded immediately, thereby causing micro-movements with physiological measures accelerating osseo-integration in the surface regions of the first type of the body part 1.2 and later of the pin part 1.1. Such dental implants thus shorten the treatment time even more than the implants according to FIGS. 1 to 3. The same is applicable for implants designed for implantation in bones other than jawbones.

Figure 6:
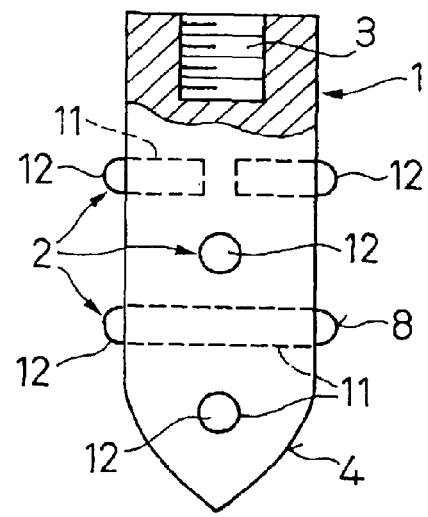
FIG. 6 shows a further essentially pin-shaped embodiment of an implant according to the invention (e.g. dental implant), the implant comprising a central and a peripheral implant part (side view)

FIG. 6 shows a further, pin-like embodiment of the implant according to the invention (e.g. dental implant, implant for fixation of bone fractures, implants for fixing support plates, shaft of artificial joint), the implant comprising a central implant part 1 and a peripheral implant part 2. The central implant part 1 comprises through-openings and/or non-through openings 11 for intergrowth with bone tissue in which openings, for example, pins 12 of the liquefiable material are inserted projecting beyond the surface of the central implant part 1 and held firmly by a friction fit. The pins 12 together form the peripheral implant part 2, the ends of the pins projecting out of the openings 11 over the surfaces 8 of the second type.

Figure 7:
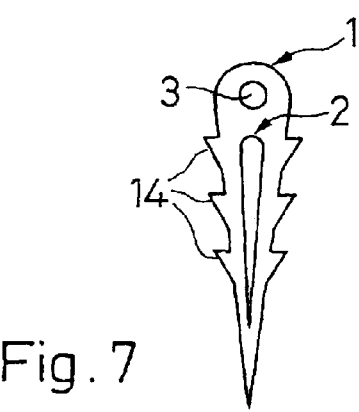
FIGS. 7 and 8 show an exemplary embodiment of an implant according to the invention, the implant being shaped as an anchor (FIG. 7: side view.
Figure 8:
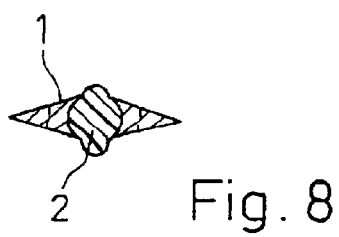

FIGS. 7 and 8 show in a side view and in cross section an anchor-shaped embodiment of the implant according to the invention. The fixation location 3 of this embodiment is for example formed as an eyelet. The anchor has a per se known shape and comprises a slot running over its length, in which slot a pin of the liquefiable material (peripheral implant part 2) is arranged with a positive fit. The pin 13 projects on both sides beyond the surface of the anchor. The anchor-shaped implant, as known such anchor implants, may comprise additional barbs 14 which on loading in tension are pressed into the bone tissue such supplementing the positive-fit anchoring by the peripheral implant part 2. However, such barbs or similar retention means are by no means necessary.

The design of the anchor edges as cutter blades simplifies implantation without the use of a suitable opening in the bone tissue or in an opening that only concerns the cortical bone.

Figure 9:
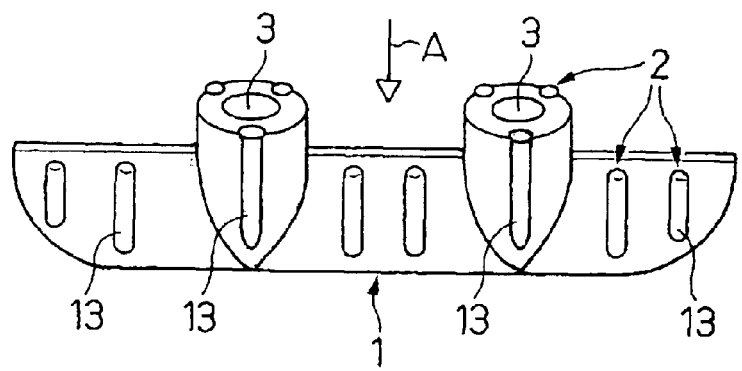
FIGS. 9 and 10 show an exemplary embodiment of a plate-shaped, diskshaped or blade-shaped implant according to the invention (e.g. dental implant with two fixation locations) as a side view (FIG. 9) and a plan view (FIG. 10)
Figure 10:
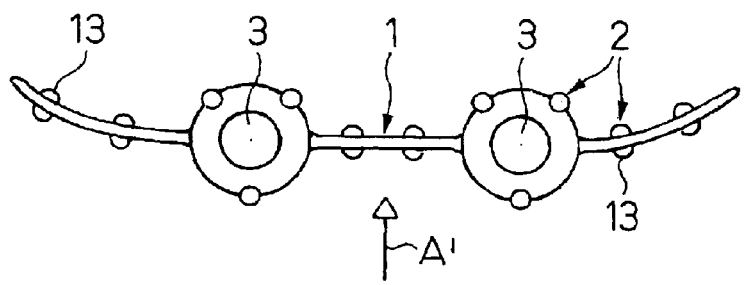

FIGS. 9 and 10 show as a further exemplary embodiment of the implant according to the invention a plate-shaped, disk-shaped, or blade-shaped dental implant that, for example, comprises two fixation locations 3 or two artificial tooth crowns and whose peripheral implant part 2 consists of a plurality of pin-like. parts 13 that are positioned in through openings in the plate, disk, or blade and in the region of the fixation locations in grooves of the central implant part.

The plate-, disk- or blade-shaped dental implants of which one example is shown in FIGS. 9 and 10 are positioned in the jaw from the jaw ridge the same as pinshaped dental implants during application of mechanical oscillation (implantation direction A, FIG. 9). However, they may also be implanted into the jawbone from the side (implantation direction A', FIG. 10), for which implantation a part of the jawbone is removed and repositioned after implantation.

Plate-, disk- or blade-shaped implants are not applicable only in the dental field but also in the orthopedic field, for which they comprise suitably equipped proximal regions.

Figure 11:
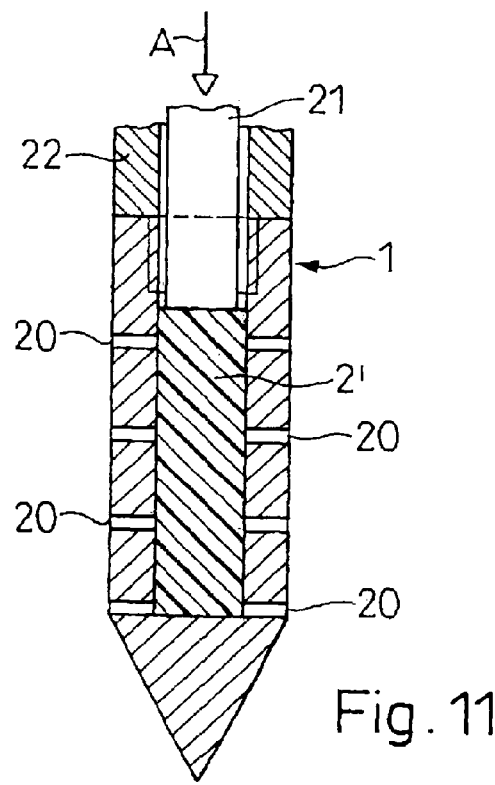
FIGS. 11 and 12 show an exemplary embodiment of a substantially pinshaped implant according to the invention (e.g. dental implant), the implant comprising a hollow central implant part (FIG. 11: longitudinal section.
Figure 12:
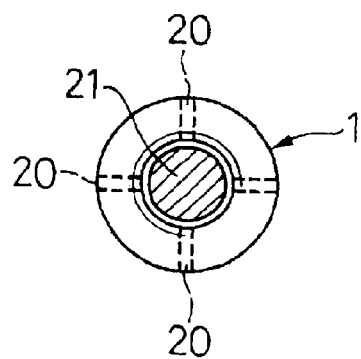

FIGS. 11 and 12 show a further pin-shaped embodiment of the implant according to the invention (e.g. dental implant or implant for orthopedic application) in a longitudinal section and as a plan view. The central implant part 1 is designed as a sleeve having an inner space 2', in which the liquefiable material is contained. The sleeve wall comprises through openings or slots 20 that, for example, are arranged in axial rows or extend axially. The implant is positioned in a bone cavity and an oscillating element 21 (sonotrode of an ultrasound apparatus) is placed onto the liquefiable material in the inner space 2' of the central implant part applying the oscillation to this material and simultaneously pressing it towards the distal implant end. By way of the oscillations the material is liquefied and by way of the pressure it is pressed through the openings or slots 20 into surface unevennesses and pores of the surrounding bone tissue, thereby creating the positive fit for primarily stabilizing the implant.

If the central implant part 1 is provided with a chisel-like, distal end, as shown, the implant according to FIGS. 11 and 12 can also be driven into the bone tissue (at least cancellous bone) without the need of an opening. An annular sonotrode 22 is suitable for this. Sonotrode 21 is applied as soon as the implant has reached the predefined position in the bone.

In an implant according to FIGS. 11 and 12 the peripheral implant part is actually created only when the implant is positioned in the bone tissue, i.e. it is created in situ.

The liquefiable material which is provided in the inner space 2' of the central implant part may be a thermoplastic material like liquefiable material arranged on the outside of a central implant part. Advantageously, however, the liquefiable material is a polymer or hydraulic cement having thixotropic properties, which cement is curable after implantation by, for example, ultraviolet light, heat, mechanical oscillations or simply with time.

When using a thermoplast as a liquefiable material being provided in an inner space 2' of the central implant part, energy directors may have to be arranged on the inner surfaces of the central implant part 1 or on the surfaces of the thermoplast.

The liquefiable material of the implant according to FIGS. 10 and 11 may be introduced in the central implant part 1 by the manufacturer or by the surgeon. It is introduced as any number of individual portions or it may be pressed through the sonotrode essentially continuously into the central implant part 1.

Figure 13:
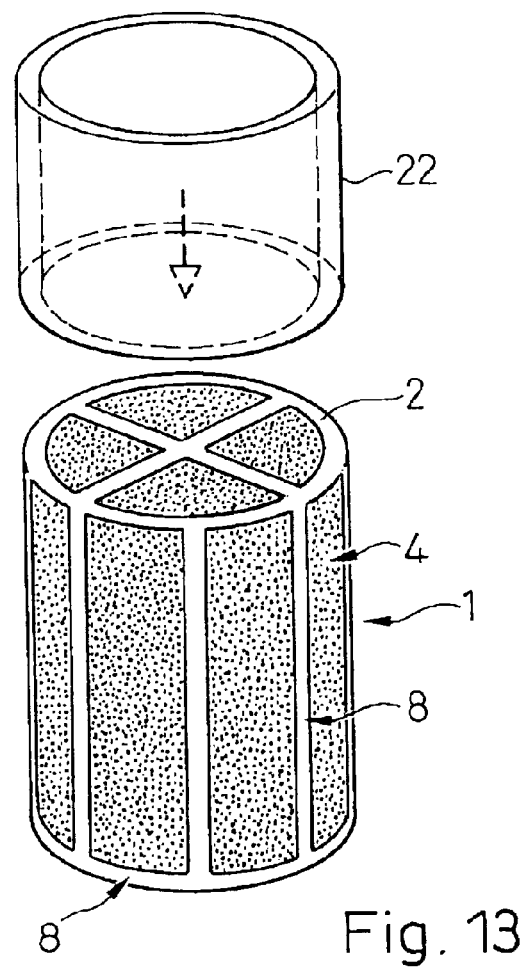
FIG. 13 shows an exemplary embodiment of the implant according to the invention, the implant comprising a central implant part with no relevant mechanical stability.

FIG. 13 shows a further exemplary embodiment of the implant according to the invention. In contrast to the implants according to the preceding Figs., this implant is not designed for a load bearing function, but rather for releasing a therapeutically effective compound, for drainage, for electric or chemical stimulation of tissue or organs, or for a similar function.

The peripheral implant part consists at least partly of the liquefiable material (surface regions 8 of the second type) and is designed as a cage having sufficient stability for implantation. The central implant part, which does not have any load bearing function, is arranged inside the cage. The implant is positioned in a bone cavity and the oscillation energy is applied to the implant it by a device (sonotrode of an ultrasound device) that is adapted to the proximal face of the implant. The sonotrode to be used for the implant according to FIG. 13 has the form of a hollow cylinder.

The central implant part constituting the surface regions 4 of the first type of the implant according to FIG. 13 has e.g. an osseo-integrative function and consists e.g. of highly porous calcium phosphate, of bone chips (patient's own cancellous bone), or of a gel. This central part may also be a device by which particles or molecules are released to the surrounding tissue (delivery device) or are removed from surrounding tissue (drainage device) or a stimulator, wherein the device is, for example, designed as a correspondingly permeable container comprising walls that constitute the surface regions 4 of the first type.

The cage according to FIG. 13 may be furnished with a central implant part by the manufacturer, or it may be filled with bone chips or the like in the operating theatre. It is also possible to implant the cage in an empty configuration and furnish it in situ with a central implant part, wherein a covering element holding the central implant part in place may be positioned and fixed by ultrasonic welding in situ also.

Figure 14:
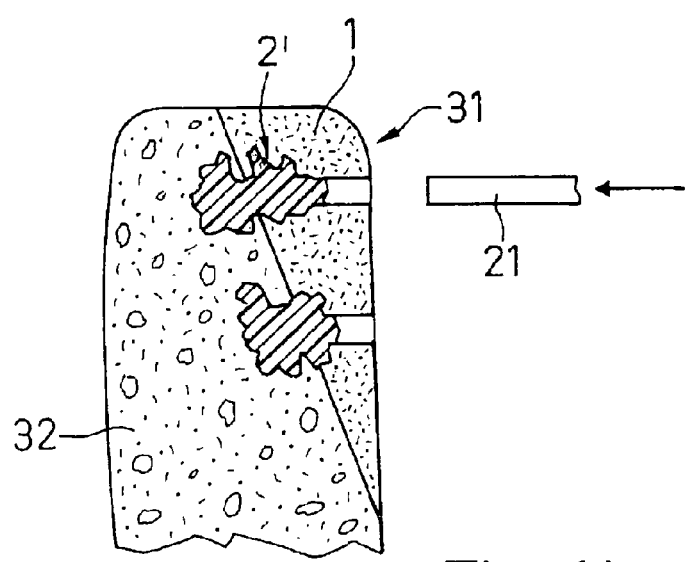
FIG. 14 shows an augmentation element as a further example of the implant according to the invention.

FIG. 14 shows as a further example of the implant according to the invention an augmentation element 31, which is applicable for producing bone tissue desirable in addition to the natural bone tissue, e.g. for enlarging the ridge 32 of a jawbone. This ridge 32 and the augmentation element 31 are shown in section and in a condition after implantation. The augmentation element 31 comprises a central implant part 1 consisting of a bone growth promoting material, e.g. of a highly porous calcium phosphate. Pins of the liquefiable material are arranged in through holes (inner spaces 2') of the central implant part 1. For implantation the augmentation element 31 is positioned on the suitably prepared jawbone ridge 32, such that the pins are directed against the ridge 32. Then using a sonotrode 21 adapted to the cross section of the pins, oscillation energy is applied to the pins while the pins are pressed towards the ridge 32. Therewith the liquefiable material is at least partly liquefied and pressed into the bone tissue jawbone ridge and into the material of the augmentation element in order to fasten the augmentation element 31 pointwise to the jawbone ridge 32 and bringing the central implant part 1 (surface regions of the first type) into intensive contact with the bone tissue of the jawbone ridge, such enabling immediately after implantation infiltration of the central implant part with cells originating from the natural bone tissue for promoting bone formation. In this case, the liquefiable material is advantageously resorbable.

FIGS. 15A to 15C and 16A to 16C show two embodiments of the implant according to the invention, applicable for connecting two vertebrae. Again the implants comprise a central implant part 1 constituting a load bearing support 1.3 and a body 1.4 arranged inside the support and equipped for being penetrated by regenerating bone tissue. The body 1.4 consists of highly porous calcium phosphate, bone chips, or a gel. The central implant part is adapted in form to a natural spinal disk and comprises on its upper and lower side ridges 40 extending in implantation direction A and fitting into grooves which have to be formed in the bone tissue of the vertebrae.

The peripheral implant part 2 is in the embodiment according to FIG. 15 arranged on the ridges 40 and in the embodiment according to FIG. 16 the material for the peripheral implant part is provided in inner spaces 2' of the central implant part 1, which in the region of the ridges 40 comprises openings 20.

Figure 15A:
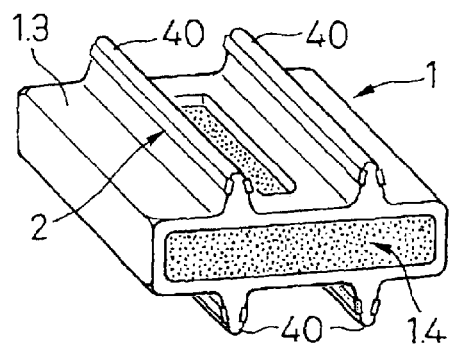
FIGS. 15 and 16 (A, B and C of each) show two embodiments of implants serving for connecting two spinal vertebrae, in three dimensional illustrations (FIGS. 15A and 16A), during implantation between the two vertebrae in a side view (FIGS. 15B and 16B), and when implanted as a front view (FIGS. 15C and 16C).
Figure 15B:
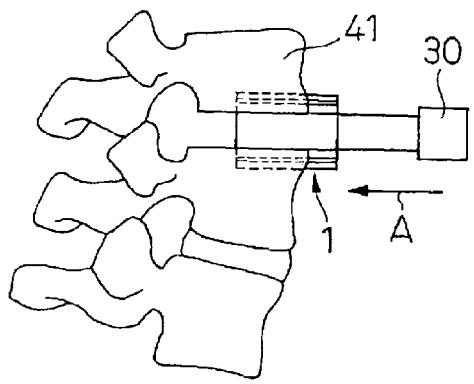
Figure 15C:
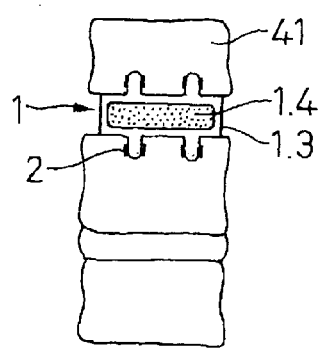

The implant according to FIG. 15A is pushed with a sonotrode 30 between two suitably prepared vertebrae as shown in FIG. 15B, wherein the liquefiable material of the peripheral implant part 2 is liquefied and pressed into the bone tissue of the vertebrae so as to anchor the implant, as shown in FIG. 15C. The sonotrode used for implantation is substantially adapted to the proximal face of the implant.

Figure 16A:
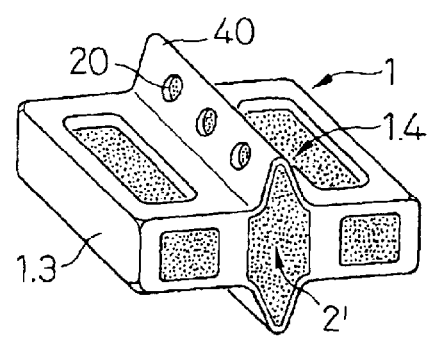
Figure 16B:
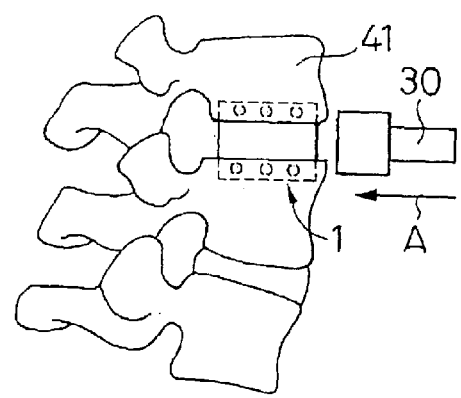
Figure 16C:
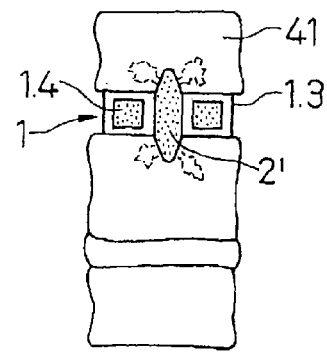

The implant according to FIG. 16A is positioned between two vertebrae as shown in FIG. 16B, e.g. using a sonotrode 30 being adapted substantially to the proximal face of the load bearing support 1.3 of the central implant part 1. When the implant is positioned, oscillation energy is applied to the liquefiable material using a sonotrode adapted to the proximal face of the inner space 2'. Therewith the material is pressed through the openings 20 and into the bone tissue of the vertebrae 41 so as to anchor the implant to the vertebrae, as shown in FIG. 16C.

The implants according to FIGS. 15 and 16 are fixed to the vertebrae immediately after implantation (primary stabilization). Therefore, it is not necessary to stabilize the two vertebrae as known in similar prior art procedures. This makes the implants particularly suitable for minimally invasive operations.

What is claimed is:

1. An implant for implantation in human or animal bone tissue or in bone tissue supplemented with bone substitute material, wherein at least a part of the implant surface is adapted to comes into contact with the bone tissue, wherein said part of the implant surface comprises surface regions (4) of a first type and surface regions (8) of a second type being different from the surface regions (4) of the first type, wherein the surface regions (8) of the second type comprise a material which is liquefiable by mechanical oscillation and with the aid of which on implantation by mechanical oscillation the implant is stabilized at least primarily in the bone tissue, wherein the surface regions (8) of the first type are equipped for a further clinical function being different from the function of primary stabilization and wherein the surface regions (4, 8) of the first type and of the second type are dimensioned and arranged in a manner such that the surface regions of the first type remain at least partly free from liquefied material on implantation by mechanical oscillation.

2. The implant according to claim 1, wherein the clinical function of the surface regions (4) of the first type, which function is different from primary stabilization, comprises osseointegration, permeation of particles or molecules out of the implant into bone tissue surrounding the implant or out of bone tissue surrounding the implant into the implant or electric or chemical stimulation.

3. The implant according to claim 1, wherein the liquefiable material is a material with thermoplastic properties or with thixotropic properties.

4. The implant according to claim 3, wherein the liquefiable material is a polymer based on lactic acid and/or glycolic acid, a polyhydroxy alkanoate, a polycaprolactone, a polysacharide, a polypeptide, a polydioxanone, a polyanhydride, a polyolefin, a polyacrylate, a polymetacrylate, a polycarbonate, a polyamide, a polyester, a polyurethane, a polysulphone, a polyarylketone, a polyimide, a polyphenyl sulphide, a liquid crystal polymer, a polyacetal, a halogenated polmer, in particular a halogenated polyolefin, a polyphenylene sulphide, a polysulphone, or a polyether or a copolymer or blended polymer of the said polymers or a composite material containing one of said polymers, or a polymeric, ceramic or hydraulic cement.

5. The implant according to claim 1, wherein the surface regions (4) of the first type comprise structures suitable for being ingrown or grown through by vital bone tissue.

6. The implant according to claim 5, wherein the surface regions (4) of the first type further have inflammation-inhibiting, infection-combating and/or growth-promoting properties.

7. The implant according to claim 1, wherein the surface regions (4, 8) of the first and of the second type are arranged beside each other and in parallel to an implantation direction (A).

8. The implant according to claim 1, comprising a central implant part (1) constituting the surface regions (4) of the first type and a peripheral implant part (2) being arranged on the outside of the central implant part, consisting at least partly of the liquefiable material and constituting the surface regions (8) of the second type.

9. The implant according to claim 8, wherein the surface regions (8) of the second type protrude at least locally over the surface regions (4) of the first type.

10. The implant according claim 1, comprising a central implant part (1) constituting the surface regions (4) of the first type and comprising an inner space (2') in which the liquefiable material is arranged or arrangeable, wherein the inner space (2') is connected to the outside of the central implant part (1) by openings (20) which are dimensioned for pressing the liquefiable material when liquid through and which are arranged in an area in which the surface regions (8) of the second type are to be produced.

11. The implant according to claim 7, wherein the implant has a load bearing function and the central implant part (1) constitutes the load bearing element of the implant.

12. The implant according to claim 11, wherein the central implant part (1) consists at least partly of a metal, a metal alloy, a ceramic material, a polymer or a composite material.

13. The implant according to claim 11, wherein the central implant part (1) comprises selfcutting or grooving elements.

14. The implant according to claim 11, wherein the central implant part (1) comprises a load bearing part (1.1) and a body part (1.2) having a variable shape.

15. The implant according to claim 11, wherein the central implant part (1) comprises a load bearing support (1.3) and a body (1.4).

16. The implant according to claim 15, wherein body (1.4) comprises a bone substitute material, bone chips or a gel.

17. The implant according to claim 8, wherein the peripheral implant part (2) is equipped for being a load bearing implant part.

18. The implant according to claim 17, wherein the central implant part (1) is a container having permeable walls or consists of a bone substitute material, of bone chips or of a gel.

19. The implant according to claim 1, being a dental implant and comprising at least one fixing location (3) or at least one crown part.

20. The implant according to claim 1, being equipped for an orthopedic application.

21. The implant according to claim 19, being pin-shaped, plate-shaped, disk-shaped or blade-shaped or having a shape being adapted or adaptable to the shape of a predetermined cavity in a bone.

22. The implant according to claim 20, being equipped for connecting two bone parts or for fixing a support plate or for serving as a shaft of a prosthesis for a hip joint, finger joint, knee joint, or shoulder joint.

23. The implant according to claim 1, having the shape of a spinal disk and comprising on its lower and upper side at least one ridge (40), wherein the surface regions (8) of the second type are arranged in the area of the ridges (40).

24. The implant according to claim 20, being pin-shaped, plate-shaped, disk-shaped or blade-shaped or having a shape being adapted or adaptable to the shape of a predetermined cavity in a bone.

25. A method for implanting an implant in bone tissue or in bone tissue supplemented with bone substitute material, the method comprising the steps of:
   providing an implant having an implant surface of which at least a contact part is adapted to come into contact with the bone tissue, wherein said contact part of the implant surface comprises surface regions of a first type and surface regions of a second type that are different from the surface regions of the first type, wherein the surface regions of the second type comprise a material that is liquefiable by mechanical oscillation, and wherein the surface regions of the first type are equipped for a further clinical function that is different from the function of primary stabilization;
   positioning the implant on or in the bone tissue;
   applying mechanical oscillation to the implant and at the same time pressing the implant against the bone tissue, thereby liquefying at least part of the liquefiable material and pressing the liquefied material into unevenesses and pores of the bone tissue;
   re-solidifying the liquefied material to form a connection with the bone tissue for primarily stabilizing the implant in the bone tissue;
   wherein the surface regions of the first and second type are dimensioned and arranged in a manner such that the surface regions of the first type remain at least partly free from liquefied material when mechanical oscillation is applied to the implant and the implant is pressed against the bone tissue; and
   wherein the surface regions of the second type are equipped and arranged for the further clinical function taking effect on the bone tissue immediately after the step of re-solidifying.

26. The method according to claim 25, wherein the implant is loaded immediately after the step of re-solidifying.

27. The method according to claim 25, wherein before the step of positioning, an opening suitable for positioning the implant is produced in the bone tissue.

28. The method according to claim 27, wherein the bone comprises a cortical part and a cancellous part underneath the cortical part, wherein the opening is produced in the cortical part and wherein the step of applying and pressing comprises advancing the implant into the cancellous part.

29. The method according to claim 25, wherein the implant is positioned on the bone tissue and the step of pressing comprises pressing the implant in a self cutting manner into the bone tissue.

30. The method according to claim 25, wherein before the step of positioning, unevenesses of a suitable geometry are produced in the bone tissue, into which unevenesses the liquefied material is to be pressed.

31. The method according to claim 25, wherein the step of applying and pressing comprises positioning a sonotrode of an ultrasound device on a proximal face of the implant.

32. The method according to claim 25, wherein the implant has the form of a cavity in the bone tissue and is implanted in this cavity.

33. The method according to claim 32, wherein the cavity is created by extracting a natural tooth root from a jaw bone.

34. The method according to claim 25, wherein the step of providing comprises combining two implant parts of two different materials to form the implant.

35. The method according to claim 25, wherein after the step of re-solidifying a further implant part is fixed on a proximal end of the implant.

36. The method according to claim 25, wherein the implant is designed for connecting two vertebrae and the step of applying and pressing comprises pushing the implant between the two vertebrae.

37. A method for implanting an implant in bone tissue or in bone tissue supplemented with bone substitute material, the method comprising the steps of:
   providing an implant having an implant surface of which at least a contact part is adapted to come into contact with the bone tissue, wherein said contact part of the implant surface comprises surface regions of a first type and surface regions of a second type that are different from the surface regions of the first type, wherein the surface regions of the second type comprise openings to an inside cavity of the implant, the inside cavity containing a material which is liquefiable by mechanical oscillation, and wherein the surface regions of the first type are equipped for a further clinical function that is different from the function of primary stabilization;
   positioning the implant on or in the bone tissue;
   applying mechanical oscillation to the implant and at the same time applying a force to the liquefiable material in the cavity, thereby liquefying at least part of the liquefiable material and pressing the liquefied material through the openings in the surface regions of the second type and into unevenesses and pores of the bone tissue;
   re-solidifying the liquefied material to form a connection with the bone tissue for primarily stabilizing the implant in the bone tissue, wherein the surface regions of the first and second type are dimensioned and arranged in a manner such that the surface regions of the first type remain at least partly free from liquefied material when the mechanical oscillation is applied to the implant and the liquefied material is pressed through the openings; and wherein the surface regions of the second type are equipped and arranged for the further clinical function taking effect on the bone tissue immediately after the step of re-solidifying.

38. The method according to claim 37 wherein the implant is loaded immediately after the step of re-solidifying.

39. The method according to claim 37, wherein before the step of positioning, an opening suitable for positioning the implant is produced in the bone tissue.

40. The method according to claim 39, wherein the bone comprises a cortical part and a cancellous part underneath the cortical part, wherein the opening is produced in the cortical part and wherein the step of applying and pressing comprises advancing the implant into the cancellous part.

41. The method according to claim 37, wherein the implant is positioned on the bone tissue and the step of pressing comprises pressing the implant in a self cutting manner into the bone tissue.

42. The method according to claim 37, wherein before the step of positioning, unevenesses of a suitable geometry are produced in the bone tissue, into which unevenesses the liquefied material is to be pressed.

43. The method according to claim 37, wherein the step of applying and pressing comprises positioning a sonotrode of an ultrasound device on a proximal face of the implant.

44. The method according to claim 37, wherein the implant has the form of a cavity in the bone tissue and is implanted in this cavity.

45. The method according to claim 44, wherein the cavity is created by extracting a natural tooth root from a jawbone.

46. The method according to claim 37, wherein the step of providing comprises combining two implant parts of two different materials to form the implant.

47. The method according to claim 37, wherein after the step of re-solidifying a further implant part is fixed on a proximal end of the implant.

48. The method according to claim 37, wherein the implant is designed for connecting two vertebrae and the step of applying and pressing comprises pushing the implant between the two vertebrae.

* * * * *